US00PP33325P2

(12) United States Plant Patent
Bedard

(10) Patent No.: US PP33,325 P2
(45) Date of Patent: Aug. 10, 2021

(54) GRANDIFLORA ROSE PLANT NAMED 'WEKPUPMOBALIP'

(50) Latin Name: *Rosa hybrida*
Varietal Denomination: WEKpupmobalip

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/247,216

(22) Filed: Dec. 3, 2020

(51) Int. Cl.
*A01H 5/02* (2018.01)
*A01H 6/74* (2018.01)

(52) U.S. Cl.
USPC ..... Plt./130
CPC ..... *A01H 6/749* (2018.05)

(58) Field of Classification Search
USPC ..... Plt./130
CPC ..... A01H 6/749; A01H 5/02
See application file for complete search history.

(56) References Cited

U.S. PATENT DOCUMENTS

| | | | |
|---|---|---|---|
| PP11,384 | P | 5/2000 | Carruth |
| PP21,605 | P2 | 1/2011 | Bedard |
| PP22,171 | P3 | 10/2011 | Austin |
| PP31,861 | P2 | 6/2020 | Carruth |

OTHER PUBLICATIONS

"Baby Love Shrub Rose", https://eu.davidaustinroses.com/products/baby-love, 4 pages, accessed Feb. 19, 2021.
Weeks Roses, "All Dressed Up", Wholesale Rose Catalog, 86 pages, 2019.

*Primary Examiner* — Keith O. Robinson
(74) *Attorney, Agent, or Firm* — McKee, Voorhees & Sease, PLC

(57) ABSTRACT

A new variety of Grandiflora rose suitable for garden decoration, having flowers of gold suffused with pink coloration.

1 Drawing Sheet

Classification: The present invention relates to a new *Rosa hybrida* plant.

Variety denomination: The new plant has the varietal denomination 'WEKpupmobalip'.

BACKGROUND OF THE INVENTION

This invention relates to a new and distinct variety of Grandiflora Rose. It has a non-disseminated seedling of my creation as its seed parent with the following genetic origin Pumpkin Patch x (Moonstone x Baby Love) and as its pollen parent the variety known as 'WEKjucistwe' (U.S. Plant Pat. No. 31,861).

SUMMARY OF THE INVENTION

Among the features which distinguish the new variety from other presently available and commercial rose cultivars known to the inventor are the following combinations of characteristics: its elegant old-fashioned flowers of gold suffused with pink coloration, its strong fruity and spices fragrance and its excellent color stability throughout the life of the flower. The plant has an upright somewhat spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKpupmobalip' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKpupmobalip' bears very double flowers (about 54 to 146 petals) of gold suffused with pink coloration, the non-disseminated seedling bears double flowers of soft orange coloration with significantly lesser petalage (about 24 to 28 petals). The new variety bears flowers with a strong fruity and spices fragrance, whereas the seed parent bears flowers with a light tea fragrance.

The new variety may be distinguished from its pollen parent, 'WEKjucistwe' by the following combination of characteristics: whereas 'WEKpupmobalip' bears medium to large sized flowers (about 8.3 to about 10.7 cm. in diameter) of gold suffused with pink coloration, 'WEKjucistwe' bears significantly smaller flowers (about 7.0 to about 9.0 cm. in diameter) of yellow blushing pink coloration. The new variety bears very double flowers (about 54 to 146 petals), whereas the pollen parent bears flowers with significantly lesser petalage (about 45 to 65 petals).

COMPARISON WITH THE CLOSEST COMMERCIALLY AVAILABLE CULTIVAR

The new variety may be distinguished from its closest commercially available cultivar, 'AUSnyson' (U.S. Plant Pat. No. 22,171) by the following combination of characteristics: whereas 'WEKpupmobalip' bears medium to large sized flowers (about 8.3 to about 10.7 cm. in diameter) of gold suffused with pink coloration, 'AUSnyson' bears significantly smaller flowers (about 7.5 cm. in diameter) of salmon-pink coloration with a golden-yellow reverse. The new variety bears flowers with a strong fruity and spices fragrance, whereas the closest commercially available cultivar bears flowers with a strong tea fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

Flower: The new variety usually bears its flowers singly, sometimes in clusters of two to five per stem. Flowers may be borne in regular rounded clusters on strong somewhat short to medium length stems (about 23 to about 44 cm.). The cluster ranges from about 16.0 to about 20.2 cm. in diameter. Outdoors, the plant blooms abundantly and nearly continuously during the growing season. The flowers have a strong fruity and spices fragrance.

Bud: The peduncle is about 1.4 to about 6.2 cm. in length, of average to somewhat heavy caliper (about 0.2 to about 0.4 cm. in diameter), and usually erect. It is somewhat rough, with few stipitate glands. Peduncle color is between 146C and 146B sometimes lightly suffused, especially on the side exposed to the sun, with between 187B and 187C. Before the calyx breaks, the bud is about 1.2 to about 1.6 cm. in diameter at the widest point, about 1.4 to about 1.8 cm. in length, and moderately ovoid to somewhat pointed in shape. The surface of the bud bears between 8 to 12 foliaceous appendages with few stipitate glands and numerous hairs, usually with stout much cut foliaceous parts extending beyond the tip of the bud about ¾ or more of its length. Bud color is between 137C and 137B. The sepals are 5 per flower, about 1.8 to about 4.4 cm. in length and about 0.8 to about 1.2 cm. in width at the widest point. The outer surface color of the sepal is between 137C and 137B. The outer surface of the sepal is mostly smooth and bears between 0 to 5 foliaceous appendages with few stipitate glands and numerous hairs. The inner surface color of the sepal is near 146C broadly bordered by near 137B. After the sepals open, the inner surface color is often lightly suffused, especially on the area exposed to the sun, with between 187B and 187A. The inner surface of the sepal is covered with fine wooly tomentum; sepal margins are entire and lined with few stipitate glands and numerous hairs. The sepals are fugacious, and usually straight in shape with acute apices. The receptacle of the flower is of somewhat short to medium length (about 0.4 to about 0.9 cm.) and average in caliper (about 0.7 to about 1.2 cm. in diameter). The receptacle is cup-shaped in form. Its surface is smooth with somewhat thick fleshy walls. The receptacle color is between 144A and 137C. As the petals open (after the calyx breaks), the bud is about 1.5 to about 2.8 cm. in diameter at the widest point, about 1.8 to about 2.6 cm. in length, and globular to somewhat ovoid in form. The color of the under surfaces of the newly opened petals is between 1C and 13C often heavily blushed on the outermost petals with between 53A and 60A. There is no visible change in coloration at the point where the petal attaches. The color of the upper surfaces of the newly opened petals is between 48A and 51B. At the point where the petal attaches, there is a large zone of between 154C and 1B.

Bloom: When fully open, the bloom ranges from about 8.3 to about 10.7 cm. in diameter. Petalage is very double with about 54 to 146 petals and about 14 to 126 petaloids irregularly arranged. When partially open, the bloom form is moderately high centered to somewhat globular to cupped, and the petals are moderately tightly spiraled to cupped with petal edges somewhat reflexed outward. When fully open, the bloom form is more cupped, and the petals are loosely cupped to somewhat undulated with petal edges somewhat reflexed outward.

Petals: The substance of the petals is heavy and of medium to somewhat thick thickness, with upper surfaces moderately satiny and under surfaces slightly shiny. The petals are about 2.3 to about 5.5 cm. in length and about 1.7 to about 4.7 cm. in width at the widest point. Petal margins are entire. The outer petals are moderately obovate to somewhat rounded in shape with rounded apices. The inner petals are broadly obovate in shape with rounded apices. Petaloids are about 0.6 to about 4.2 cm. in length and about 0.4 to about 3.1 cm. in width at the widest point. Petaloids are irregularly shaped moderately obovate to somewhat oblanceolate to subulate with rounded to sometimes lacerated apices.

Newly opened flower: The under surface color of the outer and intermediate petals is between 10D and 19C. There is no visible change in coloration at the point where the petal attaches. The upper surface color of the outer and intermediate petals is between 4C and 3D often moderately suffused with between 68C and 50A. There is no visible change in coloration at the point where the petal attaches. The under surface color of the inner petals is between 10D and 19C. The upper surface color of the inner petals is between 4C and 3D often heavily suffused with between 64D and 50A. The under and upper surface colors of the petaloids are similar in coloration to the upper and under surfaces of the inner petals. The general tonality of the newly opened flower is between 4C and 3D often heavily suffused with between 64D and 50A.

Three-day-old flower: The under surface color of the outer, intermediate and inner petals is between 8D and 19C. There is no visible change in coloration at the point where the petal attaches. The upper surface color of the outer, intermediate and inner petals is between 4D and 2D often moderately suffused with between 68C and 51B. There is no visible change in coloration at the point where the petal attaches. The under and upper surface colors of the petaloids are similar in coloration to the upper and under surfaces of the intermediate and inner petals. The general tonality of the three-day-old flower is between 4D and 2D often moderately suffused with between 68C and 51B. On the spent bloom, the petals usually drop off cleanly. In November in Wasco, Calif., blooms on the bush growing outdoors generally last about four to five days. Cut roses from plants grown outdoors and kept at normal indoor living temperatures generally last about four to five days.

Male reproductive organs: Stamens are many in number (average about 95) and are arranged regularly about the pistils; some are mixed with petaloids. The filaments are of somewhat short to medium length (about 0.4 to about 1.0 cm.) most with anthers. Filaments are between 6B and 5A in color. The anthers are moderately small for the class and all open approximately at the same time. Anther color when immature is near 22A on the external part and near 10D on the internal part. Anther color at maturity is near 164A on the external part and near 200A on the internal part. Pollen is abundant and between 18B and 16D in color.

Female reproductive organs: Pistils vary in number (average about 165). The styles are moderately uneven, average to somewhat long in length (about 0.4 to about 1.1 cm.), thin in caliper, and loosely bunched to somewhat separated. Stigma color is between 12A and 13B. Style color is between 1D and 154D often heavily suffused with between 60A and 60B. Ovaries are usually all enclosed in the calyx. The ovaries are of small size and between 158A and 158B in color. Hips are of moderately short to average length (about 1.2 to about 1.7 cm.), flat at the top and moderately globular in form, and between 31A and 30A in color when ripe. The hip surface is smooth with somewhat thin fleshy walls. The seeds are irregularly rounded, smooth in texture, approximately 25 to about 36 per hip, about 0.4 to about 0.6 cm. in diameter at the widest point and between 164C and 161B in color.

Foliage: The compound leaves are usually comprised of three to seven leaflets and are borne abundantly. The seven-leaflet leaves are about 7.6 to about 14.8 cm. in length and about 5.2 to about 10.4 cm. in width at the widest point, moderately leathery to somewhat crisp in texture on both sides, and glossy in finish on the upper side and semi-glossy in finish on the under side. The leaves have a pinnate venation pattern. The terminal leaflets are about 2.8 to about 6.2 cm. in length and about 2.5 to about 4.2 cm. in width at the widest point, shaped moderately rounded to somewhat ovate with moderately acute to somewhat cuspidate apices and moderately cordate to somewhat rounded bases. Their margins are usually simply serrate. The upper surface color of the mature leaf is between 139A and 137A. The under surface color of the mature leaf is between 146A and 147B. The under and upper colors of the leaf veins on the mature leaf are similar in coloration to the upper and under surfaces colors of the mature leaf. The upper surface color of the young leaf is between 137B and 137C, often heavily suffused with between 187A and 187B. The under surface color of the young leaf is between 146B and 147B, often heavily suffused with between 187A and 187B. The under and upper colors of the leaf veins on the young leaf are similar in coloration to the upper and under surfaces colors of the young leaf. The rachis is about 4.6 to about 8.7 cm. in length, about 0.1 to about 0.15 cm in width at the widest point, and rough. The upper side is deeply grooved with few hairs and stipitate glands on the edges of the grooves. The under side of the rachis is rough with very few stipitate glands and small prickles. The rachis color is near 146C on the under side and near 137C on the upper side, often heavily suffused on the young leaves with near 187B. The stipules are about 0.9 to about 1.6 cm. in length and of medium width (about 0.3 to about 0.8 cm.) with moderately short straight points that usually turn out at an angle of more than 45 degrees and sometimes recurve toward the stem. The under and upper surface color of the stipule is between 137A and 137B. The upper and under surfaces of the stipules are smooth in texture. The petiole is somewhat light in caliper and rough. The upper side is deeply grooved with few hairs and stipitate glands on the edges of the grooves. The under side of the petiole is rough with very few stipitate glands and small prickles. The petiole is about 0.2 to about 1.1 cm. in length and 0.1 to about 0.15 cm in width at the widest point. The petiole color is near 146C on the under side and near 137C on the upper side, often heavily suffused on the young leaves with near 187B. The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, Calif. The plant's winter hardiness and drought/heat tolerance are yet to be determined.

Growth: The plant has an upright somewhat spreading medium height growing habit (about 115 to about 150 cm. in height and about 66 to about 85 cm. spread at the widest point), with full branching. It displays moderately vigorous growth and the canes are of somewhat light to medium size caliper for the class (about 1.1 to about 1.8 cm. in diameter at the widest point). The color of the major stems is between 146C and 146B. The major stems are rough in texture and they bear some large prickles that are about 0.6 to about 1.0 cm. in length. The large prickles are angled moderately downward with a long somewhat broad oval base; prickle color is near 165B often moderately suffused with between 201B and 201C. The major stem bears few small prickles of similar shape and coloration. The color of the branches is between 146B and 137B. The branches are rough in texture and they bear some large prickles which are of similar size and shape to the large prickles on the major stems; prickle color is between 166A and 165A. The branches bear few small prickles of similar shape and coloration. The color of the new shoots is between 146C and 146B sometimes lightly suffused with near 187B. The new shoots are rough in texture and they bear some large prickles which are of similar size and shape to the large prickles on the major stems; prickle color is near 152C often moderately suffused with between 187B and 187C. The shoots bear few small prickles of similar shape and coloration.

I claim:

1. A new and distinct Grandiflora rose plant of the variety substantially as described and illustrated herein.

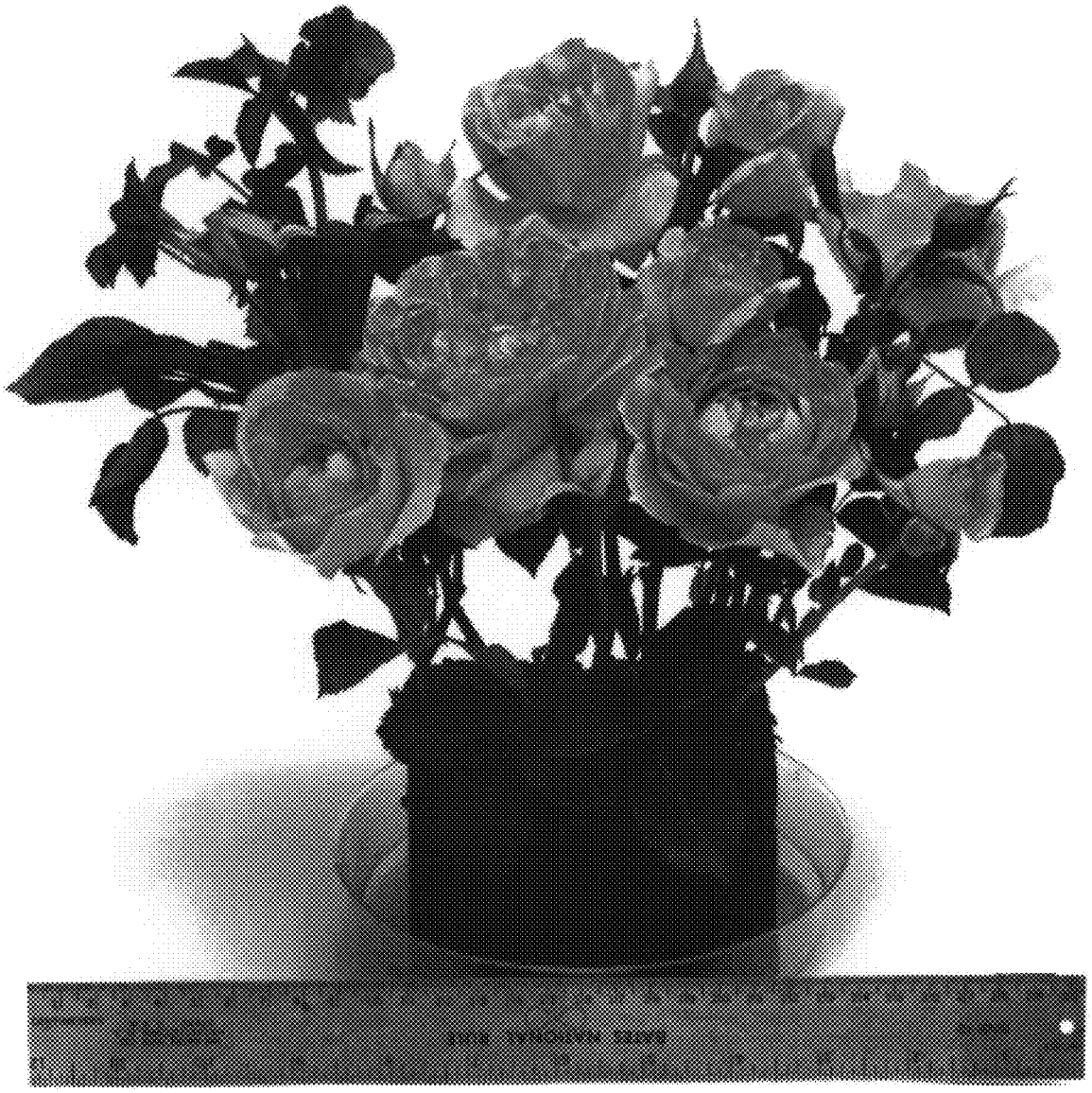

* * * * *